Aug 7, 1951 H. C. SWIM Plant Pat. 1,029
ROSE PLANT
Filed April 3, 1950
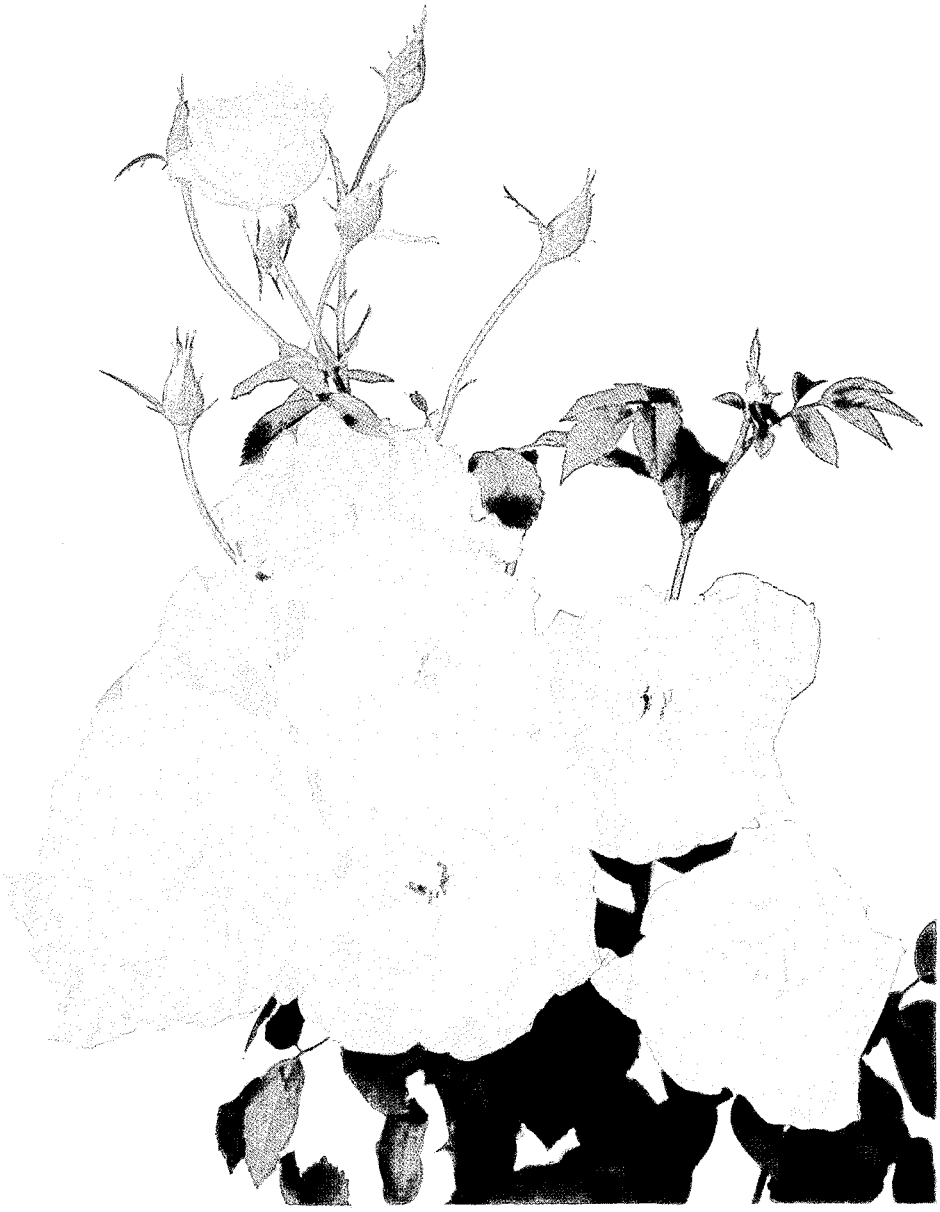
Inventor
H. C. Swim
By: Robert Cobb
Attorneys Patented Aug. 7, 1951 Plant Pat. 1,029

UNITED STATES PATENT OFFICE 1,029

ROSE PLANT

Herbert C. Swim, Ontario, Calif., assignor to Armstrong Nurseries, Inc., Ontario, Calif., a corporation of California Application April 3, 1950, Serial No. 153,628

1 Claim. (Cl. 47—61)

The present invention relates to a new and distinct variety of rose plant of the polyantha class, originated by crossing the variety "China Doll" (Plant Patent No. 678) and the variety "World's Fair" (Plant Patent No. 362), and resulting in a combination of bright red color of the flowers which are borne in broad, loose and graceful flower sprays, greater frequency of bloom, and a dwarf, semi-spreading habit of growth which is unique, and distinguishes the new variety from other polyantha roses.

This new variety most nearly resembles its seed parent "China Doll" in general appearance of the plant, but differs therefrom in the following important respects: the plant growth of the new variety is much more loose and graceful, and is almost twice as tall and twice as broad; the trusses of bloom are broader, though not as compact; the individual flowers are slightly larger and have fewer but broader petals; and the color of the flower is bright Rose Red, whereas the flower color of "China Doll" is China Rose.

As compared with its pollen parent "World's Fair," the distinctions in the new variety are equally prominent, as evidenced by the following characteristics: in habit of growth, the new variety is shorter and more bushy, with a lighter green, glossy foliage which is resistant to mildew and sufficiently abundant to give the plant a more compact appearance; the flower color is a lighter, brighter red and free from unsightly fading; the trusses in which the flowers are borne are very much larger in size; and it is endowed with a more free-blooming trait.

All of these characteristics together provide a unique combination which has not been found to exist, so far as I am aware, in any other polyantha rose, and make the new variety especially adapted for use as a dwarf hedge.

Asexual reproduction of this new variety by budding at Ontario, California, shows that the foregoing characteristics come true to form and are established and transmitted through succeeding propagations.

The accompanying drawing shows specimens of the new variety in various stages of development of the flowers and foliage.

The following is a detailed description of the new variety, the color terminology being in accord with Robert F. Wilson's Horticultural Colour Chart (1941) and Ridgway's Color Standards and Nomenclature (1912), as noted.

Type: Bush; outdoor; seedling; for cut flowers and garden decoration.
Class: Hybrid polyantha.

*Flower*

Locality where grown: Ontario, California.
Flowers borne: Usually five or more to stem; in more or less regular, rounded cluster; on normal medium length stems.
Quantity of bloom: Abundant outdoors.
Continuity: Continuous during growing season.
Fragrance: Slight.
Bud:

*Peduncle.*—Average length; slender to average caliper; sometimes bending; moderately smooth, numerous gland-tipped cilia. Color—near Lettuce Green, Plate V (Ridgway's).

*Before calyx breaks.*—Size—small. Form—Medium length; pointed, with a conspicuous neck; with few, gland-tipped cilia on the surface of the bud; usually without foliaceous parts extending beyond the tip of the bud.

*As calyx breaks.*—Color—near Chrysanthemum Crimson, Plate 824, page 169 (Wilson).

*Sepals.*—Inner surface with fine, woolly tomentum; margins of alterate sepals having stipitate glands and small appendages; other margins having woolly tomentum.

*As first petal opens.*—Size—small. Form—medium length; pointed to slightly urn-shaped. Color—outside: near Tyrian Rose, Plate 24/1, page 24 (Wilson). Point of attachment near Mimosa Yellow, Plate 602/3, page 143 (Wilson); inside: near Rose Red, Plate 724, page 158 (Wilson), shaded with Chrysanthemum Crimson, Plate 824, page 169 (Wilson). A small area at base near Mimosa Yellow, Plate 602/3, page 143 (Wilson).

*Opening.*—Opens up well. Is not retarded from opening by cold, hot, wet or dry weather.

Bloom:

*Size when fully open.*—Small to average; 2½ inches to 3 inches.

*Petalage.*—Semi-double; from 17 to 20 petals; plus 4 to 5 petaloids; arranged regularly.

*Form.*—Cupped at first; becoming flat to open; petals at first somewhat cupped; becoming later, at maturity, somewhat repand.

Petals:

*Texture.*—Medium thick; moderately leathery; with inside velvety and outside satiny.

*Shape.*—Outside—obovate; apex flat; sometimes 1 to 2 notches. Intermediate—obovate; with apex flat, with sometimes 1 to 2 notches. Inside—obovate; with apex flat; sometimes with 1 or 2 notches.

*Color.*—Colors may be modified by being shaded or washed or tinted with other colors.

This description of a newly opened flower was made from a rose grown outdoors in the month of August, 1949, at Ontario, California:

*Color.—Outside petal*—Outside surface: near Tyrian Rose, Plate 24/1, page 24 (Wilson). At base is a small area of Mimosa Yellow, Plate 602/3, page 143 (Wilson). Inside surface—near Rose Red, Plate 724/1, page 158 (Wilson). Point of attachment is near Mimosa Yellow, Plate 602/3, page 143 (Wilson. *Intermediate petal*—outside surface: near Tyrian Rose, Plate 24/1, page 24 (Wilson). At base is a small area of Mimosa Yellow, Plate 602/3, page 143 (Wilson); inside surface: near Rose Red, Plate 724, page 158 (Wilson), somewhat shaded with Chrysanthemum Crimson, Plate 824/3, page 169 (Wilson). At base is a small area of Mimosa Yellow, Plate 602/3, page 143 (Wilson). *Inner petal*—outside surface: near Tyrian Rose, Plate 24/1, page 24 (Wilson). At base is a small area of Mimosa Yellow, Plate 602/3, page 143 (Wilson); inside surface: near Rose Red, Plate 724, page 158 (Wilson), somewhat shaded with Chrysanthemum Crimson, Plate 824/3, page 169 (Wilson). At base is a small area of Mimosa Yellow, Plate 602/3, page 143 (Wilson).

This description was made from a rose that was open for three days outdoors in the month of August, 1949, at Ontario, California:

*Color.—Outside petal*—outside surface: near Rose Bengal, Plate 25/2, page 25 (Wilson). At base near white; inside surface: near Rose Bengal, Plate 25/1, page 25 (Wilson). Base near white. *Inside petal*—outside surface: near Rose Bengal, Plate 25/2, page 25 (Wilson). At base near white; inside surface: near Rose Bengal, Plate 25/1, page 25 (Wilson).

*General color effect.*—Newly opened flower—near Rose Red, Plate 724, page 158 (Wilson). Three days open—near Rose Bengal, Plate 25/1, page 25 (Wilson).

*Behavior.*—Drop off cleanly. Not particularly affected by cold, hot, wet, dry weather except that abnormal weather of any sort tends to increase prominence of blue pigment with increasing age of flower.

*Flower longevity.*—On bush in garden—4 to 5 days in August. Cut roses grown outdoors kept at living-room temperatures—3 to 4 days in August.

*Reproductive organs*

Stamens: Average number; arranged regularly about pistils.

Filaments: Short to medium length; most with anthers.

Anthers: Small; all open at once approximately. Color—margins of near Saffron Yellow, Plate 7/2, page 7 (Wilson). Rest of anthers near Lemon Yellow, Plate 4/3, page 4 (Wilson).

Pollen: Moderately abundant. Color—near Saffron Yellow, Plate 7/2, page 7 (Wilson).

Pistils: Average number; approximately 35 in number.

Styles: Moderately even; average length; thin to average caliper; somewhat loosely bunched.

Stigma:

*Color.*—Near Chrome Yellow, Plate 605/3, page 144 (Wilson).

*Style.*—Color near Chrysanthemum Crimson, Plate 824, page 169 (Wilson).

Ovaries: Usually most protruding from calyx.

Hips: Small size; ovoid; walls thick, fleshy.

Sepals: Permanent; moderately short, pointed reflexed. Color—inside—near Lettuce Green, Plate V (Ridgway's) occasionally tinged with Acajou Red, Plate XIII (Ridgway's), modified by heavy white tomentum; outside—near Lettuce Green, Plate V (Ridgway's).

Seeds: Very few; medium size; often only one.

*Plant*

Foliage:

*Leaves.*—Compound of usually 5 to 7 leaflets; moderately abundant; medium size; moderately leathery and semi-glossy to dull-surfaced.

*Leaflets.*—Oval, with apex acute; base round; margin simply serrate.

*Color.—Mature*—Upper surface—varies between Cress Green and Dark Cress Green, Plate XXXI (Ridgway's); under surface—near Asphodel Green, Plate XLI (Ridgway's). *Young*—upper surface—near Maroon, Plate 1030, page 185 (Wilson), shading over Lettuce Green. Plate V (Ridgway's); under-surface—near Purple Madder, Plate 1028/3, page 181 (Wilson), shading over Lettuce Green, Plate V (Ridgway's).

*Rachis.*—Average size. Upper side—grooved with many stipitate glands on edges. Under side—moderately prickly.

*Stipules.*—Medium length; medium width, with medium length broad points turning out at an angle of less than 45°.

*Disease.*—Average resistance to mildew.

Growth:

*Habit.*—Dwarf; semi-spreading.

*Growth.*—Moderately vigorous.

*Canes.*—Medium caliper.

*Main stems.*—Color—near Lettuce Green, Plate V (Ridgway's). Large prickles—few; medium length to long; almost straight but hooked slightly downward; with moderately long, narrow elliptical base. Color—Tawny, Plate XV (Ridgway's). Small prickles and hairs—none.

*Branches.*—Color—near Lettuce Green, Plate V (Ridgway's). Large prickles—few; medium length; hooked slightly downward; with moderately long, narrow base. Color—near Pale Green-yellow, Plate V (Ridgway's), shading at base into Pompeian Red, Plate XIII (Ridgway's). Small prickles and hairs—none.

*New shoots.*—Color—near Maroon, Plate 1030/2, page 185 (Wilson), shading into Lettuce Green, Plate V (Ridgway's). Large prickles—none. Small prickles and hairs—none.

I claim:

A new and distinct variety of rose plant of the hybrid polyantha class, characterized as to novelty by its dwarf and semi-spreading habits of growth, with glossy and mildew-resistant foliage which is produced in such abundance as to give the plant a compact appearance, by the non-fading bright red color of its flowers which are borne in large, broad, loose and graceful sprays, and by its free-blooming habit, substantially as shown and described.

HERBERT C. SWIM.

No references cited.